United States Patent [19]

Saville

[11] Patent Number: Plant 6,707

[45] Date of Patent: Mar. 28, 1989

[54] ROSE PLANT NAMED SAVABEG

[75] Inventor: F. Harmon Saville, Rowley, Mass.

[73] Assignee: Nor'East Miniature Roses, Inc., Rowley, Mass.

[21] Appl. No.: 117,097

[22] Filed: Nov. 5, 1987

[51] Int. Cl.[4] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new unusual bright orange and yellow bicolor miniature rose.

1 Drawing Sheet

The present invention relates to a new and distinct variety of rose plant of the miniature rose class, which was originated by my crossing as seed parent the variety known as "Zorina" (U.S. Plant Pat. No. 2,321) and as pollen parent an unnamed, unpatented seedling of my creation. The denomination of this new rose is "Savabeg".

Among the novel characteristics possessed by this new variety which distinguish it from its parents and all other varieties of which I am aware are its unusual bright orange and yellow bicolored flowers in this class of rose. Flowers are long lasting on the plant and after cutting. Asexual reproduction by budding of the new variety as performed in San Bernardino County, Calif. shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Colour Chart (RHSCC). The terminology used in color description herein refers to plate numbers in the aforementioned color chart, e.g., "40A" is plate 40A of the Royal Horticultural Society Colour Chart.

Parentage: Seedling.

*Seed parent.*—"Zorina".

*Pollen parent.*—Unnamed seedling.

Class: Miniature.

The following observations are made of specimens grown outdoors in San Bernardino County, Calif., during the month of August.

FLOWER

Blooming habit: Nearly continuous.

A. Bud:

(1) *Size.*—Medium.

(2) *Form.*—Urn shaped.

(3) *Color.*—As sepals divide, bud color (tight bud) is near Dutch Vermillion 40A with only slight yellow visible. However, after sepals fall, Lemon yellow 14C near point of petal attachment may be seen with mixed orange and yellow coloring at juncture.

(4) *Sepals.*—Longer than bud, foliated (with appendages).

(5) *Peduncle.*—Length — about one inch. Aspect — straight. Strength — erect. Color — near brownish green.

B. Bloom:

(1) *Size.*—Average size when fully expanded — about $\frac{3}{4}$ to 1 inch.

(2) *Borne.*—Singly, one to a stem.

(3) *Form.*—Flat with slightly recessed center. Petals have pointed apices and outer petals reflex and quill to points; inner petals roll under upon aging.

(4) *Petalage.*—Number of petals under normal conditions — about 35 to 45.

(5) *Color.*—After sepals fall, bud color is same as the color of the outer petal undersurface, i.e., Dutch Vermillion near 40A which is same coloring as petal edges but lower petal section toward point of petal attachment is near Lemon yellow 14C. The orange hued coloring blends into the yellow segment with mixed tones at the juncture. Petal top surface viewed from above appears between Capsicum red 33A and Dutch Vermillion 40A in the $\frac{1}{3}$ to $\frac{1}{2}$ open stage. However, top surface of individual petals is a bicolor combination of Capsicum Red 33A to Fire Red 33B and Lemon Yellow 14C usually with relatively clear color demarcation. Thus when flowers open fully distinctive yellow centers are pronounced and blooms appear as attractive bright orange yellow bicolored flowers. As flowers age, orange and orange red hues on the petals range from 45D to near Dawn Pink 49A through French rose 49D with darker tones replacing the deeper orange red areas then lightening toward 49D near the formerly yellow zones which in turn become near white in coloring upon aging. Petal undersurface of mature blooms is generally near white with pink washing and slightly deep pink tonality near petal edges. Overall appearance is a highly attractive combination of flowers ranging from bright orange to orange red to pink but generally featuring bright orange yellow bicolor blooms before aging.

C. Petals:

(1) *Texture.*—Thick.

(2) *Appearance.*—Inside velvety and outside satiny.

(3) *Form.*—Initially outer petals are broad and fan shaped with pointed apices, then reflex and roll under becoming diamond shaped.
(4) *Arrangement.*—Regularly arranged.
(5) *Petaloids in center.*—Average.
(6) *Persistence.*—Drop off cleanly.
(7) *Fragrance.*—Slight to none.
(8) *Lasting quality.*—Very long lasting quality on plant and as cut flower.

REPRODUCTIVE ORGANS

A. Stamens, filaments and anthers:
*Arrangement and color.*—Regularly arranged around styles. Color — pale greenish yellow; some filaments with reddish tones.
B. Pollen:
*Color.*—Pale yellow, near white.
C. Styles: Bunches, uneven, thin.
D. Stigmas:
*Color.*—Clear, translucent.
E. Hips: None observed.

PLANT

A. Form: Upright, compact.
B. Growth: Vigorous, uniform branching.
*Height attained.*—About 6 to 12 inches.
C. Foliage: Compound 5 leaflets.
(1) *Size.*—Medium.
(2) *Quantity.*—Abundant.

(3) *Color.*—New foliage: Upper side — near 137B. Under Side — near 138B. Old foliage: Upper side — near 137A. Under side — near to 137C.
(4) *Shape.*—Oval, pointed.
(5) *Texture.*—Upper side is leathery, under side is matte.
(6) *Edge.*—Serrate.
(7) *Serration.*—Ordinary.
(8) *Leaf stem.*—Color — brownish green. Under side — green.
(9) *Stipules.*—Medium length, slightly bearded.
(10) *Resistance to disease.*—Blackspot — Average. Mildew — Average. Rust — Average.
D. Wood:
(1) *New wood.*—Color — brownish green. Bark — smooth.
(2) *Old wood.*—Color — near 137C. Bark — smooth.
E. Thorns:
(1) *Thorns.*—Quantity (main stalk) — very few, almost none. On laterals from stalk — none. Form — thin, straight, pointed. Length — short. Color — near opaque. Position — irregular.
F. Winter hardiness: Needs protection in severe climates.

I claim:

1. A new and distinct variety of rose plant of the miniature rose class and all parts thereof, substantially as shown and described, characterized particularly by attractive bright orange and yellow bicolored flowers which are long lasting on the plant and as cut flowers.

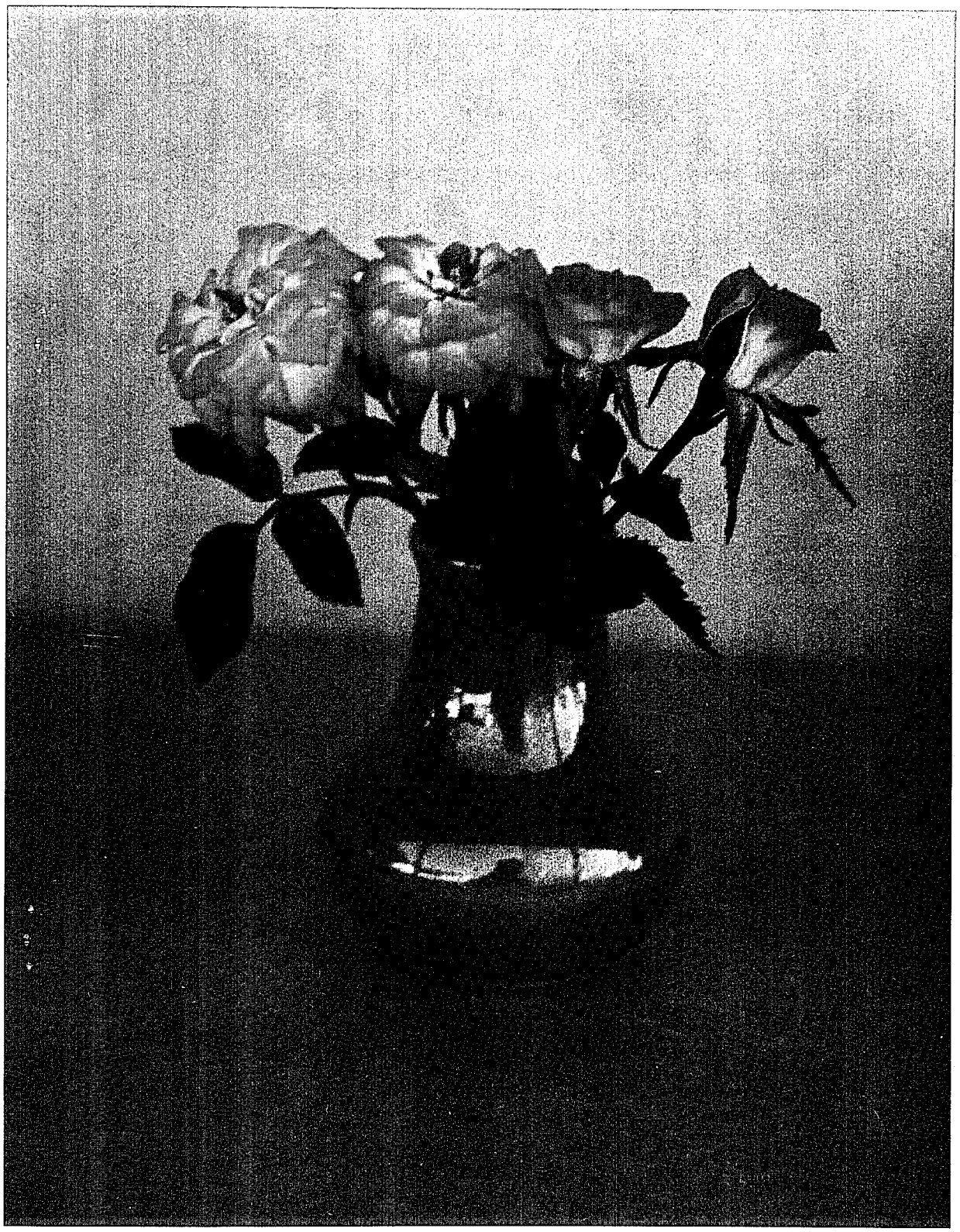

* * * * *